(12) United States Patent
Haas et al.

(10) Patent No.: US 9,242,860 B2
(45) Date of Patent: *Jan. 26, 2016

(54) PROCESS FOR THE OXIDATION OF A GAS MIXTURE CONTAINING HYDROGEN CHLORIDE

(75) Inventors: Michel Haas, Dormagen (DE); Rainer Bruns, Leverkusen (DE); Tim Loddenkemper, Dormagen (DE)

(73) Assignee: Bayer MaterialScience AG, Leverkusen (DE)

( * ) Notice: Subject to any disclaimer, the term of this patent is extended or adjusted under 35 U.S.C. 154(b) by 1647 days.

This patent is subject to a terminal disclaimer.

(21) Appl. No.: 12/150,008

(22) Filed: Apr. 24, 2008

(65) Prior Publication Data

US 2008/0269515 A1  Oct. 30, 2008

(30) Foreign Application Priority Data

Apr. 27, 2007  (DE) .......................... 10 2007 020 444

(51) Int. Cl.
  *C01B 7/04*   (2006.01)
  *C07C 263/10*   (2006.01)

(52) U.S. Cl.
  CPC ................ *C01B 7/04* (2013.01); *C07C 263/10* (2013.01)

(58) Field of Classification Search
  None
  See application file for complete search history.

(56) References Cited

U.S. PATENT DOCUMENTS

| | | | |
|---|---|---|---|
| 3,897,314 A * | 7/1975 | Liebsch et al. .................. | 203/89 |
| 4,803,065 A | 2/1989 | Itoh et al. ....................... | 423/502 |
| 5,446,196 A * | 8/1995 | Benedix et al. ............... | 560/352 |
| 5,707,919 A | 1/1998 | Miyata et al. .................. | 502/319 |
| 6,010,612 A | 1/2000 | Freire et al. .................... | 205/551 |
| 6,022,993 A | 2/2000 | Cicha et al. .................... | 562/847 |
| 6,673,960 B1 * | 1/2004 | Schwarz et al. ............... | 560/330 |
| 6,852,667 B2 | 2/2005 | Hibi et al. ...................... | 502/325 |
| 6,916,953 B2 | 7/2005 | Walsdorff et al. ............. | 560/341 |
| 2002/0028173 A1 | 3/2002 | Hibi et al. ...................... | 423/502 |
| 2004/0024244 A1 | 2/2004 | Walsdorff et al. ............. | 560/347 |
| 2004/0141901 A1 | 7/2004 | Breuer et al. | |
| 2005/0025693 A1 | 2/2005 | Bagala et al. | |
| 2005/0031529 A1 | 2/2005 | Hibi et al. ...................... | 423/502 |
| 2006/0047170 A1 | 3/2006 | Keggenhoff et al. ......... | 562/847 |
| 2006/0099138 A1 | 5/2006 | Walsdorff et al. ............. | 423/502 |
| 2009/0216042 A1 * | 8/2009 | Sasaki et al. .................. | 560/352 |
| 2009/0275776 A1 * | 11/2009 | Kasuya et al. ................. | 560/352 |

FOREIGN PATENT DOCUMENTS

| | | |
|---|---|---|
| CA | 2059281 | 10/1991 |
| EP | 0 761 593 A1 | 3/1997 |
| EP | 1170250 * | 7/2006 |

(Continued)

OTHER PUBLICATIONS

Isocyanates, Organic in Kirk Othmer Encyclopedia of Chemical Technology Copyright © 1995 by John Wiley & Sons, Inc, pp. 1-28.*

(Continued)

*Primary Examiner* — Karl J Puttlitz
(74) *Attorney, Agent, or Firm* — Donald R. Palladino; Lyndanne M. Whalen

(57) ABSTRACT

Chlorine is prepared by catalytic oxidation of a hydrogen chloride stream having a content of sulfur in elemental or bonded form of less than 100 ppm, preferably less than 50 ppm, more preferably less than 5 ppm, most preferably less than 1 ppm, based on the weight of the hydrogen chloride stream.

8 Claims, 1 Drawing Sheet

(56) References Cited

FOREIGN PATENT DOCUMENTS

| | | | |
|---|---|---|---|
| EP | 1961699 A1 | | 8/2008 |
| GB | 1046313 | | 10/1966 |
| JP | 2001-19405 | | 1/2001 |
| JP | 2004345883 | * | 12/2004 |
| JP | 2004345883 A | | 12/2004 |
| JP | 2004345884 | * | 12/2004 |
| JP | 2004345884 A | | 12/2004 |
| JP | 2005-177614 | | 7/2005 |
| JP | 20055177614 | * | 7/2005 |
| JP | 2006117528 | * | 5/2006 |

OTHER PUBLICATIONS

Machine translation of JP 2005177614.*

* cited by examiner

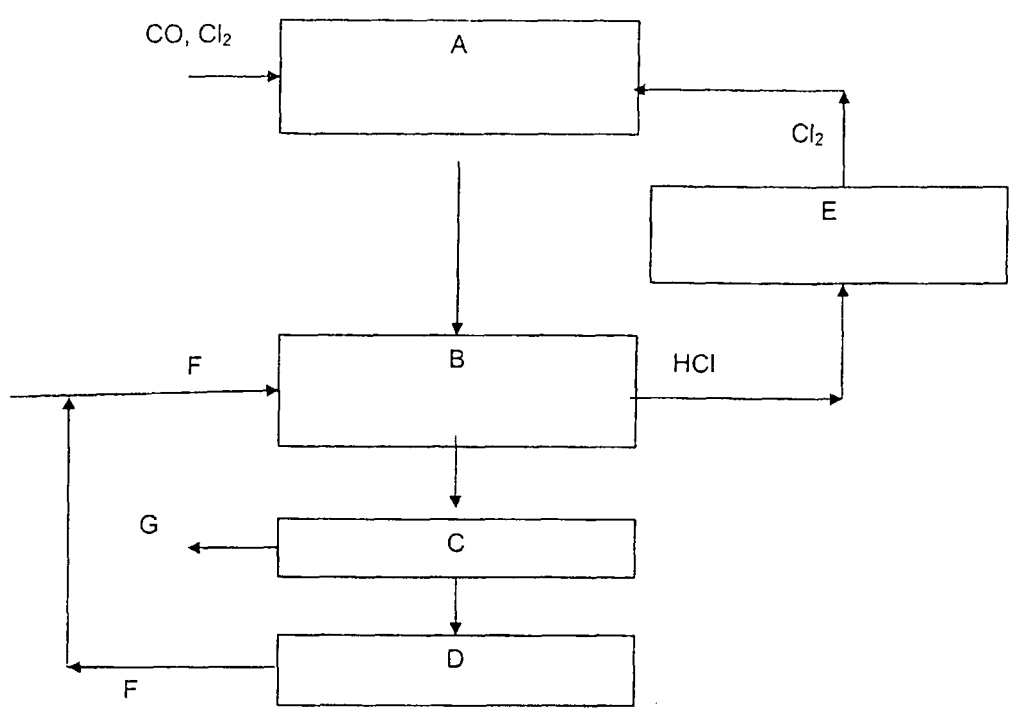

PROCESS FOR THE OXIDATION OF A GAS MIXTURE CONTAINING HYDROGEN CHLORIDE

BACKGROUND OF THE INVENTION

The present invention relates to a process for the preparation of chlorine from a gas mixture containing hydrogen chloride and further secondary components, such as sulfur compounds. The hydrogen chloride employed contains less than 100 ppm, preferably less than 50 ppm, more preferably less than 5 ppm, most preferably less than 1 ppm of sulfur in elemental or bonded form, based on the weight of the gas mixture.

A large number of chemical processes which require chlorine or phosgene as a reactant, such as the preparation of isocyanates or chlorination of aromatics, lead to an unavoidable production of hydrogen chloride. As a rule, this hydrogen chloride is converted back into chlorine by electrolysis (See, e.g., WO 97 24320 A1). Compared with this very energy-intensive method, thermal oxidation of hydrogen chloride with pure oxygen or an oxygen-containing gas over heterogeneous catalysts (the so-called Deacon process) according to $$4HCl + O_2 \Leftrightarrow 2Cl_2 + 2H_2O$$

offers significant advantages with respect to energy consumption (See, e.g., WO-A-04/0 14 845).

Catalytic oxidation of HCl gas with $O_2$ to give $Cl_2$ and $H_2O$ is typically carried out over heterogeneous catalysts. A variety of catalysts, e.g., catalysts based on ruthenium, chromium, copper etc., supported or unsupported may be used. Such catalysts are described, for example, in JP 2001 019405, DE 1 567 788 A1, EP 251 731 A2, EP 936 184 A2, EP 761 593 A1, EP 711 599 A1 and DE 102 50 313 A1. In particular, catalysts based on metallic ruthenium, ruthenium oxide, ruthenium mixed oxide, ruthenium oxychloride and ruthenium chloride, supported or unsupported, can be used. Suitable supports are e.g. tin oxide, aluminum oxide, silicon oxide, aluminum-silicon mixed oxides, zeolites, oxides and mixed oxides (e.g. of titanium, zirconium, vanadium, aluminum, silicon etc.), metal sulfates, alumina. The choice of possible supports is not, however, limited to this list.

It has now been found that sulfur components, such as $H_2SO_4$, $SO_2$, $SO_3$, $H_2S$ or COS, act as catalyst poisons. These sulfur components are gradually deposited slowly over the entire catalyst. The catalytic activity is reduced as a result. This reduced activity is unacceptable for use on a large industrial scale. The loss in activity of the catalyst can be permanent or temporary and reversible or irreversible. A further reason for the loss in activity is that most Deacon catalysts are thiophilic and therefore form more or less stable compounds with the sulfur even under very clean conditions thus rendering the catalytically active component inaccessible or deactivating it. For an optimum operation of the Deacon process, the lowest possible content of sulfur components in the HCl gas is therefore necessary.

In most processes, such as the preparation of isocyanates by phosgenation, however, considerable amount of sulfur components can be contained as an impurity in the HCl waste gas and introduced into the Deacon process. The sulfur components can have their origin in the natural gas/coal employed for the preparation of phosgene, i.e., introduction of the sulfur components into the Deacon process can take place via the CO quality in the preparation of phosgene and subsequently via the HCl process gas of the isocyanate installation. Further sources of sulfur can be present in the isocyanate process and pollute the HCl gas stream for the HCl oxidation. These additional sources of sulfur could have their origin in additives used in the isocyanate process (e.g., in the distillation), in the quality of the catalysts used (e.g., for the preparation and destruction of phosgene), and in the purity of the solvents used.

Since even the smallest amounts of sulfur can damage the Deacon catalyst reversibly or irreversibly, an expensive and comprehensive purification of the gas is to be undertaken before the isocyanate process gas comes into contact with the Deacon catalyst. This purification of the educts before they enter into the Deacon reactor is therefore essential for the life of the catalyst and accordingly for the profitability of the preparation of chlorine from HCl by catalytic oxidation.

EP 0 478 744 describes the adsorptive removal of $SO_2$ from waste gases. A purification of an HCl stream for use in a Deacon process is not described here.

JP 2005-177614 describes the removal of sulfur components from gas containing HCl or $Cl_2$. The removal is effected by bringing these gases into contact with metals or compounds thereof. The metals are chosen from groups 8-10 of the Periodic Table of the Elements.

SUMMARY OF THE INVENTION

The object of the present invention is therefore to provide a process which is as efficient as possible for reducing sulfur components in the HCl-containing process gas from an isocyanate installation which is subsequently to be fed, in particular, to a Deacon or Deacon-like process for oxidation of the hydrogen chloride with oxygen.

A further object of the present invention is to provide an HCl-containing process gas from an isocyanate installation having a low content of sulfur components in the HCl-containing process gas for a subsequent Deacon or Deacon-like process for oxidation of the hydrogen chloride with oxygen.

These and other objects which will be apparent to those skilled in the art are accomplished by catalytic oxidation of hydrogen chloride to obtain chlorine having a sulfur content of less than 100 ppm. This low sulfur-content chlorine may then be used to produce isocyanates.

BRIEF DESCRIPTION OF THE DRAWING

FIG. 1 is a schematic representation of a preferred process for producing isocyanates in accordance with the present invention.

DETAILED DESCRIPTION OF THE INVENTION

The present invention relates to a process for the preparation of chlorine by catalytic oxidation of hydrogen chloride, in which the hydrogen chloride stream employed has a content of sulfur in elemental or bonded form of less than 100 ppm, preferably less than 50 ppm, more preferably less than 5 ppm, most preferably less than 1 ppm, based on the weight of the hydrogen chloride stream.

In this context, the concentration stated in ppm is based on the weight of the sulfur-containing hydrogen chloride stream.

The gas which contains hydrogen chloride and sulfur and is employed in the process according to the invention is in general the process gas of a phosgenation reaction for the formation of organic isocyanates, but alternatively it can also be process gases from chlorination of hydrocarbons reactions.

The present invention also relates to a process for the preparation of isocyanates by phosgenation of the corresponding amines, in which a) carbon monoxide is reacted with chlorine to give phosgene, and
b) at least one amine is reacted with phosgene to yield the isocyanate(s), a crude isocyanate mixture and a gas stream containing hydrogen chloride, and
c) the crude isocyanate mixture is purified by distillation, to obtain the isocyanate and a mixture containing isocyanate and non-vaporizable residue in contents of from 10 to 70 wt. % of non-vaporizable residue, based on the weight of the mixture, and
d) the mixture of isocyanate and non-vaporizable residue in contents of from 10 to 70 wt. % obtained in step c) is fed to a further working up step in which isocyanate is recovered by evaporation in a kneader dryer or in residue pans or the amine is recovered by hydrolysis of the residue, and recycling at least a portion of the isocyanate obtained or of the amine obtained to the reaction in b), and
e) chlorine is prepared by catalytic oxidation from the gas stream containing hydrogen chloride obtained in step b), the content of sulfur in elemental or bonded form in the gas stream containing hydrogen chloride employed in the catalytic oxidation being in total less than 100 ppm, preferably less than 50 ppm, more preferably less than 5 ppm, most preferably less than 1 ppm, based on the weight of the gas stream employed, and
f) the chlorine prepared in step e) is recycled at least in part into the preparation of phosgene in step a).

The hydrogen chloride gas reacted in accordance with the present invention, which contains sulfur compounds, can include other constituents, such as hydrocarbons, CO, $CO_2$, nitrogen components etc.

Sulfur in elemental form is sulfur which is in the form of molecules containing exclusively sulfur. "Sulfur in bonded form" as used herein means compounds or molecules which, in addition to sulfur, also contain atoms other than sulfur (e.g., hydrogen sulfide, COS and sulfur salts). "Total sulfur" as used herein means sulfur and sulfur in bonded form.

The analytical determination of the sulfur content can be carried out by chromatography, in particular gas chromatography, and is preferably coupled with mass spectrometry. Alternatively, on enrichment of the sulphur compounds may be achieved on an absorbent with subsequent analysis of the absorbent for sulfur.

The preparation of phosgene from carbon monoxide and chlorine in step a) of the above-described process is known. See, for example, EP-B-881 986 or EP-A-1640341. The reaction of the carbon monoxide is carried out by reaction of the carbon monoxide with chlorine to give phosgene, for example, over an active charcoal catalyst. However, alternative catalysts can also be employed. Reference may be made here to the prior art (e.g., DE 3327274; GB 583477; WO 97/30932; WO 96/16898; and U.S. Pat. No. 6,713,035). On an industrial scale, phosgene is usually prepared by reaction of carbon monoxide with chlorine, preferably over active charcoal as the catalyst. The highly exothermic gas phase reaction is carried out at temperatures of from at least 100° C. to not more than 600° C., as a rule in tube bundle reactors. The heat of reaction can be removed in various ways, for example, by a liquid medium heat exchanger (described, e.g., in WO 03/072237), or by evaporative cooling via a secondary circulation with simultaneous use of the heat of reaction to generate steam (disclosed, e.g., in U.S. Pat. No. 4,764,308). Preferably, active charcoal is employed as the catalyst in step a). The active charcoal preferably has a total sulfur content of less than 1 wt. %, more preferably, less than 0.5 wt. %, based on the total weight of the catalyst. Furthers step a) of the present invention is preferably carried out at temperatures of less than or equal to 300° C. in combination with the generation of steam. The catalyst used in step a) preferably has a specific surface area of greater than 10 $m^2/g$.

The use of the preferred catalyst for the preparation of phosgene under the preferred conditions in step a) leads to a significantly reduced introduction of sulfur components into the hydrogen chloride-containing process gas from step b), which is reacted to give chlorine in a catalytic oxidation reaction in step e) and thus renders possible a significantly prolonged life of the catalyst employed in step e).

The preparation of isocyanates by phosgenation of primary amines and the subsequent purification of the crude isocyanate by distillation are generally known. Primary amines can be used for the process according to the invention in step b). Amines, in particular diamines, based on aliphatic or cycloaliphatic hydrocarbons having 1 to 15 carbon atoms are particularly suitable. Preferred amines are 1,6-diamino-hexane (HDA), 1-amino-3,3,5-trimethyl-5-aminomethylcyclohexane (IPDA) and 4,4'-diaminodicyclohexylamine. 1,6-Diamino-hexane is particularly preferred. Aromatic amines can also be used in the process of the present invention. Examples of preferred aromatic amines are toluenediamine (TDA), in particular 2,4-TDA and 2,6-TDA and mixtures thereof, diaminobenzene, naphthyldiamine (NDA) and 2,2',2,4'- or 4,4'-methylenediphenyldiamine (MDA) or isomer mixtures thereof. Toluenediamine (TDA), in particular 2,4-TDA and 2,6-TDA and mixtures thereof, is preferred. 2,2'-, 2,4'- or 4,4'-methylenediphenyldiamine (MDA) and mixtures thereof are also preferred.

The reaction of amines with phosgene is known in principle and described, for example, in Ullmann's Encyclopedia of Industrial Chemistry, 5th ed. vol. A 19 p. 390 et seq., VCH Verlagsgesellschaft mbH, Weinheim, 1991 and G. Oertel (ed.) Polyurethane Handbook, 2nd edition, Hanser Verlag, Munich, 1993, p. 60 et seq., and G. Wegener et al., Applied Catalysts A: General 221 (2001), p. 303-335, Elsevier Science B.V.

Preferably, the reaction of the amine, for example, TDA and phosgene in step b) takes place as follows: TDI is prepared from TDA by reaction with phosgene in process step b). The TDA preferably originates from the hydrogenation of dinitrotoluene (DNT). Process step b) is also called phosgenation herein. The phosgenation reaction is carried out with the formation of hydrogen chloride as a by-product.

The synthesis of isocyanates in general and of TDI in particular is adequately known from the prior art. Generally, phosgene is employed in a stoichiometric excess, based on the amine, preferably TDA. The phosgenation in step b) conventionally takes place in the liquid phase (DE 3744001 C1, EP 0314985 A1). It is possible for the phosgene and TDA to be dissolved in a solvent. Preferred solvents are chlorinated aromatic hydrocarbons, such as chlorobenzene, o-dichlorobenzene, p-dichlorobenzene, trichlorobenzenes, the corresponding chlorotoluenes or chloroxylenes, chloroethylbenzene, monochlorodiphenyl, α- and β-naphthyl chloride, benzoic acid ethyl ester, phthalic acid dialkyl esters, diisodiethyl phthalate, toluene and xylenes. Further examples of suitable solvents are known from the prior art. As is moreover known from the prior art, e.g. WO-A-96/16028, the isocyanate formed can likewise itself function as a solvent for phosgene.

In another, preferred embodiment, the phosgenation takes place above the boiling point of the TDA. Gas phase phosgenation is described, e.g., in EP 570 799 A, EP 1555258 A1, EP 1526129 A1 or DE 10161384 A1. Advantages of this gas phase process over the otherwise conventional liquid phase phosgenation include energy savings due to the minimization of expensive solvent and phosgene circulation. The TDA can be reacted with phosgene in a one-stage or two-stage or optionally multi-stage reaction. In this context, a continuous and also discontinuous mode of operation is possible.

If a one-stage phosgenation in the gas phase is chosen, the reaction is carried out above the boiling temperature of the TDA, preferably within an average contact time of from 0.05 to 5 seconds and at temperatures of from 200 to 600° C. (DE 10161384 A1). If phosgenation in the gas phase is chosen, this reaction is preferably carried out adiabatically. It is also preferable for the phosgenation to be carried out in the gas phase in a tube reactor without moveable inserts with the gases preferably being led into the reactor without backmixing.

Temperatures of from 20 to 240° C. and pressures of from 1 to approx. 50 bar are conventionally employed in liquid phase phosgenation (U.S. Pat. No. 3,544,611). The phosgenation in the liquid phase can be carried out in one stage or several stages, it being possible for phosgene to be employed in a stoichiometric excess. In this context, the TDA solution and the phosgene solution are preferably combined via a static mixing element and subsequently led, for example, from the bottom upwards through one or more reaction towers, where the mixture reacts to give the desired isocyanate. In addition to reaction towers which are provided with suitable mixing elements, reaction containers with a stirring device can also be employed. Apart from static mixing elements, specific dynamic mixing elements can also be used. Suitable static and dynamic mixing elements are known from the prior art.

As a rule, continuous liquid phase preparation of isocyanate on an industrial scale is carried out in two stages. In this context, in the first stage, in general at temperatures of not more than 220° C., preferably not more than 160° C., carbamoyl chloride is formed from amine and phosgene and amine hydrochloride is formed from amine and the hydrogen chloride split off. This first stage is highly exothermic. In the second stage, the carbamoyl chloride is split into TDI and hydrogen chloride and the amine hydrochloride is converted into carbamoyl chloride. The second stage is generally carried out at temperatures of at least 90° C., preferably from 100 to 240° C.

The phosgenation is preferably carried out in the gas phase, since gas phase phosgenation in general is carried out under a higher pressure than liquid phase phosgenation and a subsequent compression of HCl before entry into the catalytic oxidation is thus simplified. The absolute pressure in the phosgenation is therefore preferably in the range of from 1 to 30 bar, more preferably from 1 to 6 bar.

The phosgenation is preferably carried out in the gas phase because the inert substances added in the gas phase phosgenation, in particular nitrogen, lead to a dilution of the hydrogen chloride-containing process gas stream for catalytic oxidation to give chlorine according to step e). The exothermic catalytic oxidation of HCl to chlorine can be controlled better and more easily in the gas phase and the removal of the heat of reaction in step e) is simplified. The addition of the inert substances into the gas phase phosgenation improves the removal of heat in step e) and thereby prevents local overheating of the catalyst thereby prolonging the life of the catalyst.

Via the solvents employed in the phosgenation in the liquid phase or gas phase, sulfur components contained in the solvents in the hydrogen chloride-containing process gas stream thereof from step b) are introduced into the catalytic HCl oxidation to give chlorine according to step e). A solvent having a total sulfur content of less than 5 ppm, preferably of less than 3 ppm, is particularly preferably employed for the phosgenation.

Another reason that phosgenation in the gas phase is preferred is that the total solvent hold-up (i.e. the total solvent quantity) in this process is significantly reduced compared with phosgenation in the liquid phase and the hold-up (quantity) of total sulfur is thus also significantly reduced. This leads to a significantly prolonged service life of the catalyst in step e).

The phosgenation in step b) is also preferably carried out in the gas phase because EP 0570799 teaches that gas phase phosgenation produces yields above 95%. The high yield leads to a lower production of non-vaporizable TDI residue mixture which has to be worked up in step d). The amount to be employed, where appropriate, in step d) of optionally sulfur-containing additives therefore decreases, and this leads to a lower content of sulfur in the hydrogen chloride-containing process gas which is oxidized catalytically to chlorine in step e). The life of the catalyst in step e) is thus prolonged by the phosgenation in the gas phase in step b).

The liquid product stream, the crude toluene-diisocyanate, is then worked up by distillation, in general in several stages, in step c). The phosgene still dissolved in the crude isocyanate mixture from step b) and the solvent are separated off, recovered and recycled to the process. The distillation of the crude isocyanate mixture in step c) can be carried out by generally known methods (as described, for example, in EP-A-1413571 and US 2003/0230476 A1). The distillation is in general carried out in several stages and is described, for example, in WO-A-2004/056757 and EP-B-1575907.

However, all the known processes for purification of the crude TDI by distillation in step c) have the common feature that in addition to the desired purified TDI from the distillation, a mixture containing toluene-diisocyanate and distillation residue is obtained which must be further treated. In this context, the separation of the TDI residue mixture, which is processed further in step d), from the bottom product streams of the particular columns can be carried out at the start, in the middle and at the end of the distillation sequence.

The recovery of the solvent in the distillation in step c) and/or in the further working up in step d) and recycling into phosgenation step b) means that sulfur components present in the solvent enter into the hydrogen chloride-containing process gas from step b), the gas stream containing hydrogen chloride, and consequently can damage the catalyst in step e). The recycling of solvent from the distillation in step c) and/or from the further working up in step d) also means that sulfur components from additives employed in step c) and/or d) are introduced via the solvent circulation into the phosgenation step b) and therefore into the hydrogen chloride-containing process gas which is oxidized catalytically in step e). Sulfur components in the additives used in step c) and/or d) can thus lead to a reduction in the life of the catalyst in step e).

In step d), the mixture obtained in step c) containing isocyanate and non-vaporizable TDI distillation residue having a content of residue of from 1 to 70 wt. %, preferably from 20 to 70 wt. %, based on the weight of the mixture, is subjected to a further working up step in order to achieve the highest possible TDI yield and to minimize the production of residual substances requiring disposal.

For this, the mixture containing isocyanate and non-vaporizable TDI residue can first be concentrated further via an evaporator to obtain additional isocyanate and fed to the distillation in step c). A mixture containing isocyanate and non-vaporizable isocyanate residue in contents of greater than 30 wt. % of non-vaporizable isocyanate residue, preferably greater than 40 wt. % of non-vaporizable isocyanate residue, based on the weight of the mixture, is obtained.

This mixture can be worked up by several possible processes.

In a first embodiment, the working up is carried out in a residue pan, i.e. in a stirred and heated container, high-boiling hydrocarbons (preferably bitumen) which are inert under the distillation conditions being mixed in so that the free isocyanate still present in the residue is distilled off as completely as possible. The residue which remains can be discharged as a free-flowing solid and fed to a combustion process, as described in EP 0548685 A2. A disadvantage of this process is that the bitumen can contain considerable amounts of sulfur compounds. These sulfur compounds can be released under the distillation conditions and are then washed out of the distillation gas stream with solvent in the subsequent washers. The solvent contaminated with the sulfur compounds is used as described above in the phosgenation according to step b) and therefore leads to a reduction in the life of the catalyst in step e). Preferably, bitumen having a total sulfur content of less than 5 wt. %, preferably virtually sulfur-free bitumen having a total sulfur content of less than 1 wt. % is employed in this embodiment.

In an alternative embodiment, the working up in step d) is carried out by using kneader dryers (U.S. Pat. No. 5,446,196). In this process, the heated and stirred containers described above are replaced by kneader dryers. By using, for example, bitumen, the residue which remains is obtained as a free-flowing solid which can be employed as a fuel, for example, in cement works. Preferably, in this embodiment bitumen having a total sulfur content of less than 5 wt. %, preferably virtually sulfur-free bitumen having a total sulfur content of less than 1 wt. % is employed.

In a further preferred embodiment, the working up in step d) is carried out using kneader dryers with at least two rotating shafts thereby eliminating use of bitumen. Suitable kneader dryers with two rotating shafts are disclosed, for example, in DE 10120391 A1.

In a further particularly preferred embodiment, the working up according to step d) is carried out by hydrolysis with water. Primary amines as employed in step b) are obtained. Residue hydrolysis is known per se and is described, for example, in WO-A-2007/007887 or WO-A-2007/007791 or U.S. Pat. No. 6,673,960. Hydrolysis is particularly preferred if the isocyanate is TDI. In a further preferred embodiment, the hydrolysis is carried out using virtually sulfur-free additives having a total sulfur content of less than 1 wt. %.

The residue contains compounds from which TDA can be recovered via hydrolysis, such as e.g. carbodiimides, ureas, uretdiones etc. Instead of the kneader dryers or residue pans, with which sulfur-containing bitumen must be employed, isocyanate and optionally hydrogen chloride and solvent can therefore first preferably be separated off in an evaporator in step d) to obtain a liquid mixture containing 30-70 wt. % isocyanate, preferably TDI, and 30-70 wt. % residue. This mixture is then worked up again in the residue hydrolysis. The hydrolysis of the residue is a reaction with water, so-called hydrolysis. Hydrolysis of the residue is in general promoted by bases or acids. The hydrolysis can be used to denature the TDI distillation residue, as described in U.S. Pat. No. 4,091,009. A further possibility is the recovery of TDA, which can then be reacted in the isocyanate process with the addition of phosgene to give TDI. Such processes are described, for example, in DE-A-29 42 678, JP-A-5 8201 751 and DE-A-19 62 598. The residue hydrolysis can be carried out both in batch processes and continuously, e.g., in a tube reactor. Preferred temperatures for carrying out the hydrolysis are in the range of from 100° C. to 280° C. and the pressure is preferably between 1 bar and 50 bar.

The hydrolysis of the distillation residue is conducted without bitumen and with low-sulfur chemicals and therefore renders possible a significant reduction in the sulfur load in the HCl waste gas for the hydrogen chloride oxidation.

In step d), the stream which essentially contains isocyanate and non-vaporizable residue is therefore reacted with water in a pressure hydrolysis. Primary amines are obtained. This process is preferred in particular for the case where the isocyanate is TDI.

A combination of the steps described, such as a residue hydrolysis with a subsequent absorptive purification of the HCl gas, is entirely suitable for reducing the sulfur load still further.

The working up of the mixture of isocyanate product and distillation residue in step d) can in principle also be dispensed with, and this mixture can be burned continuously or discontinuously. The process is technically simple and can be employed for generating usable steam if an installation suitable for this for thermal exploitation exists in the vicinity of the isocyanate production installation, in order to ensure disposal via a pipeline connection.

Recapitulating, the object of the present invention of providing a hydrogen chloride-containing process gas of an isocyanate installation for a subsequent Deacon or Deacon-like process for oxidation of the hydrogen chloride with oxygen is achieved in summary form in step d) in that the working up of the non-vaporizable TDI distillation residue in step d) can be carried out by addition of low-sulfur bitumen having total sulfur contents of less than 5 wt. %, preferably less than 1 wt. %.

The object of the present invention is furthermore achieved in that the working up of the non-vaporizable TDI distillation residue can be carried out in kneader dryers with several shafts without addition of bitumen.

The object of the present invention can furthermore be achieved in that the working up of the non-vaporizable TDI distillation residue in step d) can be carried out by hydrolysis. Preferably, virtually sulfur-free additives having a total sulfur content of less than 1 wt. % are employed.

The object of the present invention can furthermore be achieved in that working up of the non-vaporizable TDI distillation residue in step d) is dispensed with, and this residue is subjected, e.g., to a thermal exploitation, such as a combustion.

Alternatively, the HCl process gas stream from step b), the gas stream containing hydrogen chloride, can first be purified from sulfur and sulfur compounds in an absorption, an adsorption (active charcoal, adsorption agent) or a guard bed, before it enters into the HCl oxidation in step e).

In step e), chlorine is prepared from the gas stream obtained in step b) containing hydrogen chloride by catalytic oxidation, the content of sulfur in elemental or bonded form in the gas stream containing hydrogen chloride employed in the catalytic oxidation in total being less than 100 ppm, preferably less than 50 ppm, more preferably less than 5 ppm, even more preferably less than 1 ppm, in most preferably 0.001 to 1 ppm, based on the weight of the hydrogen chloride stream.

It is thus necessary for the first gas stream containing hydrogen chloride obtained in step b) to be provided in the required purity with respect to sulfur. This can be achieved by the measures described above. It may thus be necessary, where appropriate, for the gas streams containing hydrogen chloride obtained in step b) to be purified before their use in the catalytic oxidation to chlorine.

The purification of the HCl gas obtained in step b) from sulfur in elemental or bonded form cannot be carried out via a water washing step, since the HCl would be absorbed and HCl losses would therefore automatically arise. A complete absorption of the HCl in water to give hydrochloric acid, purification of the hydrochloric acid and subsequent desorption of the HCl from the aqueous hydrochloric acid is very expensive in terms of energy and offers an inadequate purification. The purification is therefore difficult.

Preferred purification methods for the HCl are adsorption processes with, e.g., active charcoal or various ceramic absorption materials, such as aluminum oxide, silicon oxide, zirconium oxide etc. and mixed oxides. Preferably, regenerable adsorption materials are used. The adsorption materials can be impregnated with metals or metal compounds. Possible compounds are, e.g., copper oxide, lanthanum oxide, zinc oxide, titanium oxide, zinc titanate, iron oxide, calcium oxide, silicate and aluminum oxide, and mixed compounds. It is also possible to employ several adsorption beds connected in series, the content of which can differ. This adsorption step can be carried out in a fixed bed or in a fluidized bed, preferably a fixed bed, in a temperature range of from 0° C. to 600° C., preferably from 20° C. to 400° C., and a pressure range which lies between 1 bar and 50 bar, preferably in the range of the HCl oxidation employed in the following step. Regeneration of the adsorption bed can be carried out by shutting off the HCl stream and subsequently introducing an inert gas, optionally with further constituents, such as oxygen or hydrogen, under elevated temperature.

A further preferred possibility is to integrate a guard bed concept. In this, the hydrogen chloride and optionally further gases, such as oxygen or chlorine or a mixture of several gases, are led over a catalyst. In this context, the sulfur components are deposited via a chemical reaction (e.g., oxidation and/or complexing). In this embodiment, a simultaneous removal of further constituents via a chemical reaction can be ensured. Thus, an oxidation of carbon monoxide, a further possible catalyst poison, and hydrocarbons, substituted and unsubstituted, in the presence of oxygen is possible. This method can be carried out both in a fixed bed reactor and in a fluidized bed reactor. Such a purification is described, for example, in JP 2005-177614.

Alternatively, the gas stream from the residue pans or kneader dryers can be purified directly from sulfur via an adsorption or guard bed, before it is fed back into the phosgenation step. This has the advantage that significantly lower amounts of gas have to be purified.

In step d), a gas stream containing isocyanate and any solvent present and any traces of sulfur compounds present is separated off from the mixture obtained in step c) containing isocyanate and non-vaporizable residue. In a preferred embodiment, the separating off of any hydrogen chloride still present from the mixture containing isocyanate and non-vaporizable residue is likewise carried out in step d). This embodiment is particularly preferred if kneader dryers or residue pans are employed in step d). Preferably, the gas stream obtained in this way containing isocyanate and any solvent is then purified to remove sulfur and sulfur compounds in an absorption or in a guard bed.

All of these methods have the common feature that they lead to a reduction in the sulfur content in the process gas of an isocyanate installation for a Deacon process. In every case, the removal of sulfur from the isocyanate process gas is an additional, often relatively expensive purification step in the Deacon process before the gas comes into contact with the catalyst. The embodiment in which the residue is worked by hydrolysis in step d) is comparatively simple.

However, it is also advantageous to influence the purity of the HCl gas of the isocyanate installation with respect to the content of sulfur components by reducing sources of sulfur in the overall isocyanate process itself. The sulfur content in the CO-containing intake stream into the preparation of phosgene in step a) is therefore preferably reduced in order to avoid contamination of the HCl waste gas stream.

A further possibility for establishing a low content of sulfur in the phosgene is, for example, the use of higher-quality educts in the preparation of phosgene, which already have a correspondingly low content of sulfur. In particular, the use of CO having a corresponding low content of sulfur, preferably below 100 ppm, more preferably below 10 ppm, most preferably below 1 ppm is suitable. Processes for the preparation of CO having a low content of sulfur are known to the person skilled in the art. Thus, for example, CO which has been obtained by gasification of coal, steam reforming, $CO_2$ reforming, partial oxidation of hydrocarbons or other processes can be employed. CO can likewise be obtained by separation from CO-containing gas mixtures. Such processes for the preparation or obtaining of CO are described e.g. in Chemische Technik (pub.: Dittmeyer, Keim, Kreysa, Oberhold), 5th ed., vol. 4, page 981-1007.

The low sulfur content required in the CO is achieved by employing raw materials which are practically sulfur-free or have a sufficiently low sulfur content for the preparation or obtaining of CO. It is irrelevant in this context how the absence of sulfur or the sufficiently low sulfur content of the raw materials for the preparation or obtaining of CO is achieved.

Another possibility for achieving the required low sulfur content in the CO is the removal of sulfur (in elemental or bonded form) from the CO to be employed. Numerous processes which serve this purpose are described in the literature. There may be mentioned by way of example the removal of sulfur-containing impurities, such as $H_2S$, in accordance with US-A1-2005/0025693, by bringing the CO-containing gas stream into contact with active charcoal which has been impregnated with a metal oxide. Another possibility is, in accordance with DE-A1-103 01 434, conversion of inorganic and organic sulfur compounds in the presence of steam over an aluminum oxide contact at elevated temperature and passing of the gas mixture obtained over a composition containing iron hydroxide in the presence of steam and defined amounts of oxygen. DE-A1-103 01 434 describes other possible methods for freeing CO from sulfur-containing impurities.

The largely sulfur-free CO obtainable in this way can then be reacted to give phosgene in the context of conventional and known processes, such as those described e.g. in Ullmanns Enzyklopädie der industriellen Chemie, 3rd ed., vol. 13, page 494-500.

A further route for obtaining phosgene having a low content of elemental or bonded sulfur is separation of elemental or bonded sulfur from the phosgene itself. Here also, in principle, all of the usual separation processes, for example, distillation, adsorption and the like can be employed. For the process of the present invention, it is critical to adhere to the above-mentioned upper limit for the concentration of elemental or bonded sulfur.

The phosgene obtained in step a) preferably has a sulfur in elemental or bonded form content of less than 100 ppm.

The process according to the invention for the preparation of chlorine by catalytic oxidation of hydrogen chloride, in which the hydrogen chloride stream employed has a content of sulfur in elemental or bonded form of less than 100 ppm, preferably less than 50 ppm, more preferably less then 5 ppm, most preferably less than 1 ppm, based on the weight of the hydrogen chloride stream, renders it possible to achieve considerably prolonged service lives of the Deacon catalyst, e.g., in the coupling with an isocyanate process, and in the case of a reversible or partly reversible poisoning process to achieve prolonged deactivation times and therefore a longer life of the catalyst.

The catalytic hydrogen chloride oxidation in the process according to the invention can be carried out adiabatically or isothermally or approximately isothermally, discontinuously, but preferably continuously as a fluidized or fixed bed process, preferably as a fixed bed process, particularly preferably in tube bundle reactors over heterogeneous catalysts at a reactor temperature of from 180 to 500° C., preferably 200 to 450° C., most preferably 220 to 400° C., under a pressure of from 1 to 25 bar (1,000 to 25,000 hPa), preferably 1.2 to 20 bar, more preferably 1.5 to 17 bar and most preferably 2.0 to 15 bar.

Conventional reaction apparatuses in which the catalytic hydrogen chloride oxidation may be carried out are fixed bed or fluidized bed reactors. The catalytic hydrogen chloride oxidation can preferably also be carried out in several stages.

In the isothermal or approximately isothermal and adiabatic procedure, several, preferably 2 to 10, more preferably 2 to 6, even more preferably 2 to 5, most preferably 2, 3 or 4 reactors connected in series with additional intermediate cooling can also be employed. The hydrogen chloride can be added either completely together with oxygen upstream of the first reactor, or distributed over the various reactors. This connection in series of individual reactors can also be combined in one apparatus.

A further preferred embodiment of a device which is suitable for the process comprises employing a supported catalyst in which the catalyst activity increases in the direction of flow. Such a supported catalyst can be effected by the method of impregnation of the catalyst support with the active composition or by different dilution of the catalyst with an inert material. Rings, cylinders or balls of titanium dioxide, zirconium dioxide or mixtures thereof, aluminum oxide, steatite, ceramic, glass, graphite, high-grade steel or nickel-containing alloys can be employed, for example, as the inert material. In the case of the preferred catalyst shaped bodies, the inert material should preferably have similar outer dimensions.

Shaped bodies having any desired shapes are suitable as catalyst shaped bodies. Tablets, rings, cylinders, stars, wagon-wheels or balls are preferred. Rings, cylinders or strands of stars are particularly preferred as the shape.

Suitable heterogeneous catalysts are, in particular, ruthenium compounds or copper compounds on support materials, which can also be doped. Doped ruthenium catalysts are preferred. Suitable support materials are, for example, silicon dioxide, graphite, titanium dioxide having the rutile or anatase structure, zirconium dioxide, aluminum oxide or mixtures thereof, preferably titanium dioxide, zirconium dioxide, aluminum oxide or mixtures thereof, most preferably γ- or δ-aluminum oxide or mixtures thereof.

The copper or the ruthenium catalysts can be obtained, for example, by impregnating the support material with aqueous solutions of $CuCl_2$ or $RuCl_3$ and optionally a promoter for doping, preferably in the form of their chlorides. The shaping of the catalyst can be carried out after or, preferably, before impregnation of the support material.

Promoters which are suitable for doping of the catalysts are alkali metals, such as lithium, sodium, potassium, rubidium and caesium, preferably, lithium, sodium and potassium, most preferably potassium, alkaline earth metals, such as magnesium, calcium, strontium and barium, preferably, magnesium and calcium, most preferably, magnesium, rare earth metals, such as scandium, yttrium, lanthanum, cerium, praseodymium and neodymium, preferably, scandium, yttrium, lanthanum and cerium, most preferably, lanthanum and cerium, or mixtures thereof.

The shaped bodies can then be dried, and where appropriate, calcined at a temperature of from 100 to 1,000° C., preferably 100 to 500° C., under a nitrogen, argon or air atmosphere. Preferably, the shaped bodies are first dried at 100 to 150° C. and then calcined at 200 to 500° C.

The conversion of hydrogen chloride in a single pass can preferably be limited to 15 to 90%, preferably 40 to 85%. Some or all of the unreacted hydrogen chloride can be recycled into the catalytic hydrogen chloride oxidation after being separated off.

The heat of reaction of the catalytic hydrogen chloride oxidation can be utilized in an advantageous manner to generate high pressure steam. This can be utilized, e.g., for operating a phosgenation reactor or distillation columns, in particular, isocyanate distillation columns.

The chlorine obtained by the process according to the invention can then be reacted with carbon monoxide at least in part by the process known from the prior art to give phosgene, which can be employed for the preparation of isocyanates from the corresponding amines. The hydrogen chloride formed in turn in the phosgenation of the amines can then be reacted by the processes described to give chlorine.

The sulfur content in the HCl stream is reduced significantly by the process of the present invention, as a result of which the service life of the Deacon catalyst in the next step is prolonged and a possible deposition of the sulfur components (due to the catalyst) leads to slower, reduced deactivation of the catalyst.

FIG. 1 is a schematic representation of a preferred embodiment of the process according to the invention for the preparation of isocyanates, in which the following symbols have the following meaning:
A: Phosgene synthesis (step a))
B: Isocyanate synthesis (step b))
C: Distillation (step c))
D: Residue hydrolysis (step d))
E: Catalytic HCl oxidation
F: Amine
G: Isocyanate The chlorine prepared in E is recycled into the phosgene synthesis in A. The amine F recovered in D is recycled into the phosgenation in B.

EXAMPLES

Example 1

10 g ruthenium chloride n-hydrate were dissolved in 34 ml water, 200 g support ($SnO_2/Al_2O_3$ (85:15 m/m)) were added and the components were mixed thoroughly until the solution had been taken up by the support. The support impregnated in this way was left to stand for 1 h. The moist solid was finally dried in unwashed form in a muffle oven for 4 h at 60° C. and 16 h at 250° C.

2 g of the dried catalyst were subjected to a gas flow of 8 l/h (STP) oxygen, 2 l/h (STP) hydrogen chloride and 10 l/h (STP) nitrogen at 300° C. The amount of chlorine formed was determined by passing into a 16% strength potassium iodide solution and titration of the iodine formed with thiosulfate. A space/time yield which was constant over time of 0.48 kg chlorine/(kg cat. h) resulted.

In further experiments, certain amounts of sulfur components were added with the aid of perfusor pumps, under conditions which otherwise remained the same. The amounts stated for the sulfur compounds in ppm relate to the total gas stream. The drop in the space/time yield (activity) of the catalyst after a poisoning time of 10 hours with $SO_2$ and COS is stated in Table 1.

TABLE 1

| Sulfur component | Amount of sulfur component (ppm) | Drop in activity in 10 h |
|---|---|---|
| $SO_2$ | 525 | 69% |
| $SO_2$ | 158 | 55% |
| $SO_2$ | 53 | 11% |
| COS | 53 | 32% |
| COS | 11 | 20% |

Example 2

Phosgene generated by reaction of carbon monoxide with chlorine over active charcoal was reacted at temperatures of greater than 300° C. in the gas phase with 2.5 tons of gaseous TDA to give crude TDI. An HCl part stream was oxidized catalytically to chlorine after purification via a low temperature cold trap. The crude TDI was purified by distillation, a TDI residue mixture with approx. 20 wt. % TDI distillation residue was obtained, which was concentrated to approx. 50 wt. % via an evaporator. Further TDI was obtained from this mixture with addition of bitumen having a sulfur content of <5 wt. %.

Example 3

A phosgene solution in ortho-dichlorobenzene (ODB) which is prepared by dissolving phosgene in ODB. The phosgene was prepared from chlorine and carbon monoxide over active charcoal with simultaneous generation of steam. This phosgene was reacted with a TDA solution in ODB to produce crude TDI. This TDI was purified by distillation and a pure TDI and a mixture of TDI with approximately 10 wt. % TDI distillation residue was obtained. This residue mixture was concentrated to 50 wt. % TDI distillation residue and, in a kneader dryer, bitumen was added continuously. Additional TDI was obtained. The vacuum exhausts of the kneader dryer were washed with ODB and the wash liquid obtained was re-used in the phosgenation. The HCl stream was purified via a low temperature cold trap operated at −35° C. and then via an absorber filled with active charcoal and, with a sulfur content of less than 1 ppm, oxidized catalytically to chlorine. 50 kg/h chlorine were obtained. The solvent used had a sulfur content of 4 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an isocyanate by phosgenation of an amine comprising:
   a) reacting carbon monoxide with chlorine to form phosgene,
   b) reacting an amine with phosgene to form, a crude isocyanate mixture and a gas stream containing hydrogen chloride,
   c) distilling the crude isocyanate mixture to purify the mixture and obtain the isocyanate and a mixture containing isocyanate and from 10 to 70 wt. % of non-vaporizable residue, based on the weight of the mixture,
   d) working up the mixture of isocyanate and 10 to 70 wt. % of non-vaporizable residue obtained in c) to recover isocyanate by evaporation in a kneader dryer or in residue pans or the amine by hydrolysis of the residue, and recycling at least a portion of the isocyanate obtained or of the amine obtained to the reaction in b), and
   e) subjecting the gas stream containing hydrogen chloride with a content of sulfur in elemental or bonded form of less than 100 ppm, based on weight of the gas stream, obtained in b) to catalytic oxidation to produce chlorine, and
   f) recycling at least a portion of the chlorine prepared in step e) to the preparation of phosgene in a).

2. The process of claim 1 in which in d), the isocyanate is separated from the residue in a kneader dryer or in a residue pan using bitumen having a sulfur content of <5 wt. % sulfur, based on total weight of the bitumen being employed.

3. The process of claim 1 in which in d), separation of the isocyanate from the residue is carried out in a kneader dryer or residue pans.

4. The process of claim 3 in which the gas stream containing hydrogen chloride from b) is purified to remove sulfur by absorption.

5. The process of claim 3 in which the gas stream containing hydrogen chloride from b) is purified in a guard bed.

6. The process of claim 1 in which CO and/or phosgene is freed from sulfur via an adsorption agent in a).

7. The process of claim 1 in which phosgene having a sulfur content of less than 100 ppm is generated in a).

8. The process of claim 1 in which the reaction of the amine with phosgene in b) is carried out in the gas phase.

* * * * *